United States Patent
Nabutovsky et al.

(10) Patent No.: US 10,179,243 B2
(45) Date of Patent: Jan. 15, 2019

(54) SYSTEMS AND METHODS FOR PROVIDING TEMPORARY INDUCED DYSSYNCHRONY THERAPY TO PATIENTS WITH ATRIAL TACHYCARDIA

(71) Applicant: PACESETTER, INC., Sylmar, CA (US)

(72) Inventors: Yelena Nabutovsky, Mountain View, CA (US); Jennifer Rhude, Carbondale, IL (US); Edward Karst, Los Angeles, CA (US); Taraneh G. Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 36 days.

(21) Appl. No.: 15/628,448

(22) Filed: Jun. 20, 2017

(65) Prior Publication Data

US 2018/0361156 A1 Dec. 20, 2018

(51) Int. Cl.
| | |
|---|---|
| *A61N 1/36* | (2006.01) |
| *A61N 1/368* | (2006.01) |
| *A61N 1/362* | (2006.01) |
| *A61N 1/365* | (2006.01) |

(52) U.S. Cl.
CPC ......... *A61N 1/3682* (2013.01); *A61N 1/3627* (2013.01); *A61N 1/3684* (2013.01); *A61N 1/3688* (2013.01); *A61N 1/365* (2013.01)

(58) Field of Classification Search
CPC .... A61N 1/3627; A61N 1/365; A61N 1/3682; A61N 1/3684; A61N 1/3688
USPC .................................................... 607/2, 4, 9
See application file for complete search history.

(56) References Cited

U.S. PATENT DOCUMENTS

| | | | |
|---|---|---|---|
| 9,539,427 B2 * | 1/2017 | Kass ..................... | A61N 1/3627 |
| 2011/0015691 A1 * | 1/2011 | Stahmann ............ | A61N 1/3622 607/14 |
| 2011/0027229 A1 * | 2/2011 | Van Antwerp ..... | A61K 31/7056 424/85.7 |
| 2011/0125208 A1 * | 5/2011 | Karst ..................... | A61B 5/029 607/17 |
| 2011/0178567 A1 * | 7/2011 | Pei ........................ | A61N 1/3622 607/25 |
| 2011/0184379 A1 * | 7/2011 | Van Antwerp ....... | A61K 38/212 604/503 |
| 2011/0270212 A1 * | 11/2011 | Van Antwerp ..... | A61K 31/7056 604/500 |
| 2012/0109247 A1 * | 5/2012 | Rajan ................... | A61N 1/3627 607/28 |
| 2013/0158619 A1 * | 6/2013 | Lee ........................ | A61B 5/686 607/17 |
| 2013/0204312 A1 * | 8/2013 | Gill ...................... | A61N 1/3627 607/18 |

* cited by examiner

*Primary Examiner* — Christopher A Flory

(57) ABSTRACT

The present disclosure provides systems and methods for providing temporary induced dyssynchrony (TID) therapy to patients with atrial tachycardia. An implantable cardiac device includes a pulse generator coupled to a plurality of electrodes, and a controller communicatively coupled to the pulse generator and configured to cause the pulse generator to apply TID therapy to a patient's heart via the plurality of electrodes, determine that the patient's heart is experiencing atrial tachycardia, and adjust at least one parameter of the TID therapy based on the determination.

20 Claims, 3 Drawing Sheets

SYSTEMS AND METHODS FOR PROVIDING TEMPORARY INDUCED DYSSYNCHRONY THERAPY TO PATIENTS WITH ATRIAL TACHYCARDIA

A. FIELD OF THE DISCLOSURE

The present disclosure relates generally to cardiac stimulation systems, and more particularly to an implantable cardiac device that provides temporary induced dyssynchrony (TID) therapy to patients with atrial tachycardia.

B. BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats, and the valves regulating blood flow may develop leaks, allowing regurgitation or backflow of blood. The impairment of arterial circulation deprives vital organs of oxygen and nutrients. Fatigue, weakness, and inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage.

Using temporary induced dyssynchrony (TID) therapy to create asynchrony in HF patients without underlying dyssynchrony has been shown to facilitate improvement of cardiac chamber function, cellular function, and cardiac reserve. Specifically, at least some known TID therapy, such as pacemaker-induced transient asynchrony (PITA) therapy that uses a pacemaker to induce asynchrony, involves using right ventricular (RV) pacing to induce forced ventricular asynchrony in a patient's heart at regular intervals (e.g., for a period of six hours every night for six weeks). One concept behind TID therapy is that the heart may benefit from "exercise" (i.e., forcing the heart into ventricular asynchrony), similar to other muscles in the body.

However, it has also been shown that TID therapy is effective when applied at regular, periodic intervals. When a patient is unable to tolerate a scheduled session of TID therapy and must cancel the session, the benefits of the TID therapy may be reduced. This may be of particular concern in patients experiencing atrial tachycardia, such as atrial fibrillation or atrial flutter. In such patients, the delivery of the TID therapy may need to be altered to achieve the desired benefits.

BRIEF SUMMARY OF THE DISCLOSURE

In one embodiment, the present disclosure is directed to an for providing temporary induced dyssynchrony (TID) therapy to patients with atrial tachycardia. The implantable cardiac device includes a pulse generator coupled to a plurality of electrodes, and a controller communicatively coupled to the pulse generator and configured to cause the pulse generator to apply TID therapy to a patient's heart via the plurality of electrodes, determine that the patient's heart is experiencing atrial tachycardia, and adjust at least one parameter of the TID therapy based on the determination.

In another embodiment, the present disclosure is directed to an implantable cardiac device having a pulse generator coupled to a plurality of electrodes. The implantable cardiac device further includes a computing device having a memory device, and a processor communicatively coupled to the memory device, the processor configured to cause the pulse generator to apply temporary induced dyssynchrony (TID) therapy to a patient's heart, determine that the patient's heart is experiencing atrial tachycardia, and adjust at least one parameter of the TID therapy based on the determination.

In another embodiment, the present disclosure is directed to a method for providing temporary induced dyssynchrony (TID) therapy to patients with atrial tachycardia. The method includes applying TID therapy to a patient's heart, determining that the patient's heart is experiencing atrial tachycardia, and adjusting at least one parameter of the TID therapy based on the determination.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for providing temporary induced dyssynchrony (TID) therapy, such as pacemaker-induced transient asynchrony (PITA) therapy, to patients with atrial tachycardia. An implantable cardiac device includes a plurality of electrodes. A controller communicatively coupled to the plurality of electrodes is configured to cause the plurality of electrodes to apply TID therapy to a patient's heart, determine that the patient's heart is experiencing atrial tachycardia, and adjust at least one parameter of the TID therapy based on the determination.

Figure 1A:
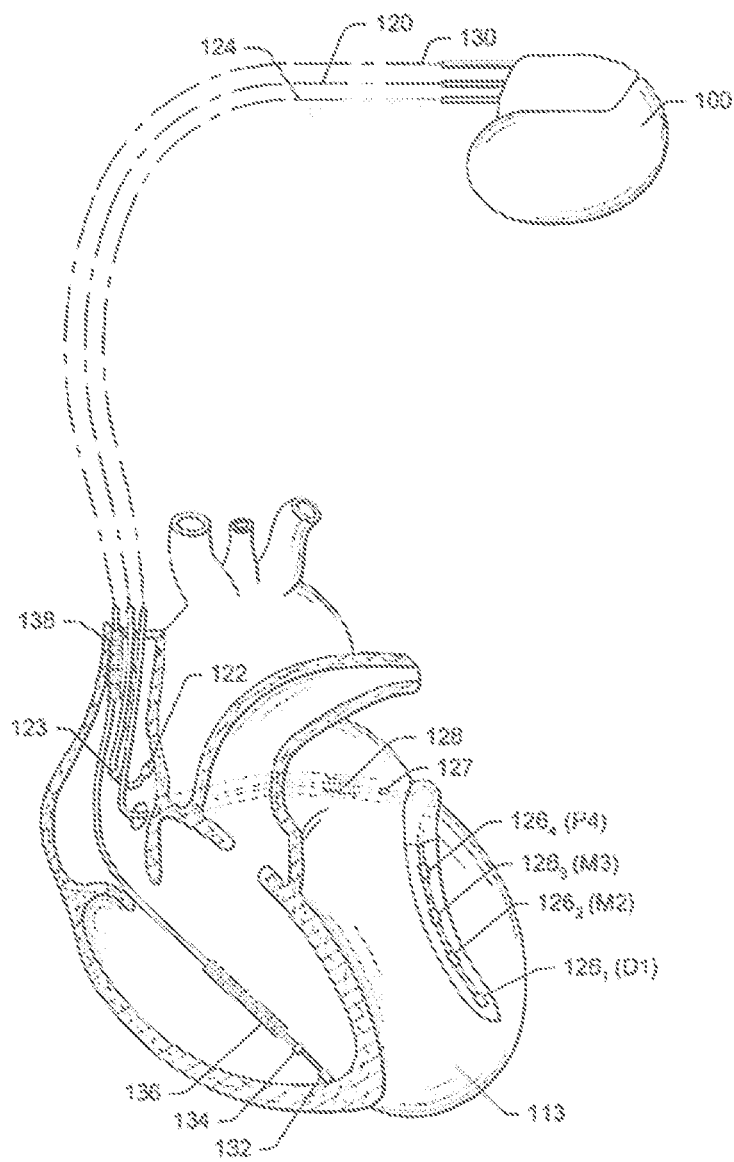
FIG. 1A is a simplified, partly cutaway view illustrating an implantable stimulation device in electrical communication with at least three leads implanted into a patient's heart for delivering multi-chamber stimulation and shock therapy and sensing cardiac activity.
Figure 1B:
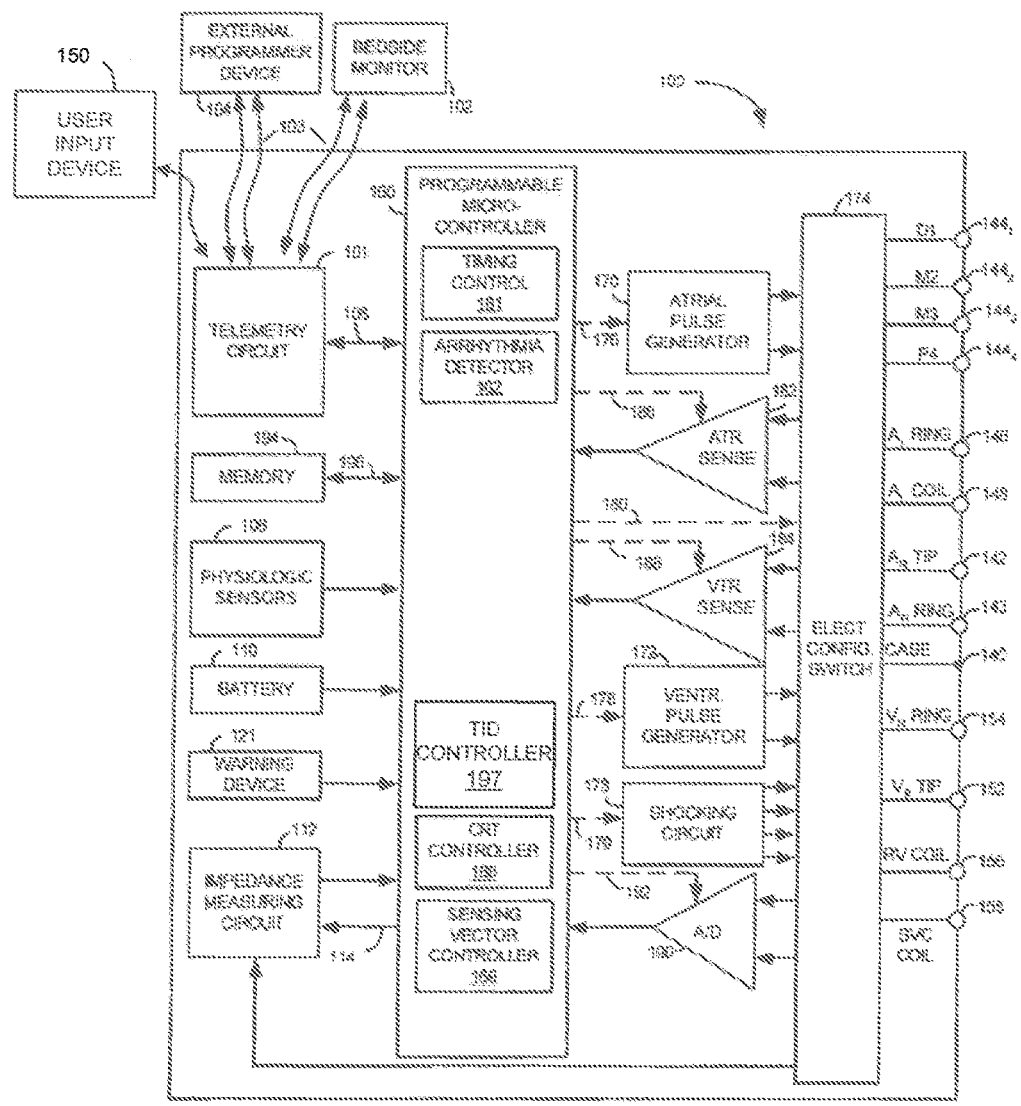
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multipoint pacing (MPP). To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by Abbott Laboratories, which includes four pacing electrodes on the left ventricular lead—enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil electrode 136). Below is a list of exemplary vectors that can be used for pacing and/or sensing using LV electrodes D1, M2, M3 and P4 with and without the RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals, 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to atrial ring electrode 123. To achieve left chamber sensing, pacing and shocking, the connector includes an LV tip terminal $144_1$ adapted for connection to the D1 electrode and additional LV electrode terminals $144_2$, $144_3$ and $144_4$ terminals adapted for connection to the M2, M3 and P4 electrodes of quadra-pole LV lead 124.

The connector also includes an LA ring terminal ($A_L$ RING) 146 and an LA shocking terminal ($A_L$ COIL) 148, which are adapted for connection to LA ring electrode 127 and the LA coil ($A_L$ COIL) electrode 128, respectively. To support right chamber sensing, pacing and shocking, the connector further includes an RV tip terminal ($V_R$ TIP) 152, an RV ring terminal ($V_R$ RING) 154, an RV shocking terminal ($V_R$ COIL) 156, and an SVC shocking terminal (SVC COIL) 158, which are adapted for connection to ventricular tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 (controlled by a control signal 176) and a ventricular pulse generator 172 (controlled by a control signal 178) generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc. Timing control circuitry 161 may also track durations of time such as TID therapy being applied, TID therapy being cancelled or paused, a patient experiencing atrial tachycardia.

Microcontroller 160 further includes an arrhythmia detector 162 that can be utilized by pacemaker/ICD 100 for determining desirable times to administer various therapies. Additional components of the microcontroller may include a cardiac resynchronization therapy (CRT) controller 168 to control CRT and a temporary induced dyssynchrony (TID) controller 197 (described in detail below).

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain IEGMs in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, CRT controller 168 and TID controller 197 may be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar (e.g., using unipolar leads in the atrium and ventricle and performing atrial sensing in a bipolar way using the ventricular lead tip as an indifferent electrode), etc.) by selectively closing the appropriate combination of switches (not shown) as is known in the art. The switch also switches among the various LV electrodes.

Atrial sensing circuits 182 (controlled by a control signal 186) and ventricular sensing circuits 184 (controlled by a control signal 188) may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190 (controlled by a control signal 192). Data acquisition system 190 is configured to acquire intracardiac electrogram signals, convert the raw analog data into a digital signal, and store the digital signals for later processing and/or telemetric transmission to an external programmer device 104 or a bedside monitor 102 or personal advisory module. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external programmer device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external programmer device 104 and/or bedside monitor 102 through an established communication link 103. Additionally, telemetry circuit 101 enable communication between microcontroller 160 and a user input device 150. User input device 150 may include any kind of user computing device, such as a mobile phone, a laptop, a tablet, a wearable computing device (e.g., a fitness wearable or "smart glasses") or may include any other kind of input device, such as a remote control or an input device specifically configured for communication with pacemaker/ICD 100 to control functionality thereof. User input device 150 may additionally or alternatively include a "smart home controller" or similar Internet of Things device. An internal warning device 121 (also referred to as a patient alert) may be provided for generating perceptible warning signals to the patient via vibration, voltage or other methods.

Pacemaker/ICD 100 further includes and/or is in communication with one or more physiologic sensors 108. Physiologic sensor 108 may include an accelerometer, and may be referred to as a "rate-responsive" sensor because it is typically used to adjust pacing stimulation rate according to the exercise state of the patient. Physiologic sensor 108 may additionally or include a blood pressure sensor, a heart rate sensor, a temperature sensor, an impedance sensor, an activity sensor, and/or a blood oxygenation sensor.

Pacemaker/ICD 100 additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 (i.e., using RV coil electrode 136 as a common electrode).

In this embodiment, microcontroller 160 further includes temporary induced dyssynchrony (TID) controller 197. TID controller 197 controls pacemaker/ICD 100 to deliver TID therapy to a patient's heart. The TID therapy facilitates improving cardiac function for a patient's heart. For patients who experience atrial tachycardia during sessions of TID therapy (i.e., induced asynchrony via RV pacing), there are several important considerations: (1) alternative ways to deliver RV pacing to the patient during an atrial tachycardia episode, (2) ability of the patient to tolerate TID therapy when they are experiencing atrial tachycardia, and (3) ensuring that the patient receives the benefit of the TID therapy. Accordingly, the systems and method described herein facilitate applying the TID therapy in patients experiencing atrial tachycardia with one or more adjustments to the TID therapy.

During periods of normal heart function (e.g., normal atrial rates), TID therapy such as PITA therapy including forced RV pacing can be applied to a patient's heart by increasing a programmed ventricular pacing rate or shortening an atrioventricular (AV) delay. When a patient experiences atrial tachycardia, they may be unable to tolerate this form of TID therapy, and with variable atrial rates, shortening AV delay may not be effective if pacing into a refractory period and even potentially pro-arrhythmic if pacing into a vulnerable period. In one embodiment, TID controller 197 is configured to determine that a patient is experiencing atrial tachycardia and, accordingly, adjust at least one parameter of the TID therapy. In some cases, TID controller 197 may identify a type of atrial tachycardia experienced by the patient. The patient may be experiencing atrial flutter, which is a regular, relatively slow tachycardia, or full atrial fibrillation (AF), which is irregular and relatively fast.

In some embodiments (e.g., when the patient is experiencing atrial fibrillation), TID controller 197 may automatically switch a pacing mode of the TID therapy, for instance, to a non-tracking ventricular pacing mode in which the ventricle is paced independent of the atrium. In some embodiments, in order to continue inducing asynchrony by forced RV pacing during atrial tachycardia, TID controller 197 may increase the ventricular pacing rate.

Additionally or alternatively, in some embodiments (e.g., when the patient is experiencing atrial flutter), TID controller 197 may reduce the shortening of the AV delay. In still other embodiments, TID controller 197 may pause or cancel TID therapy.

When a patient experiences atrial tachycardia, the patient may be unable to tolerate TID therapy (i.e., RV-only pacing). TID controller 197 is configured to receive a signal from one or more sensors (e.g., sensor 108 and/or sensing vector controller 169, shown in FIG. 1B), such as a hemodynamic sensor, that indicates the patient status. In some cases, a sensor and/or sensing lead may sense a high rate in the atrium, indicating atrial tachycardia. In other cases, one or more sensors and/or sensing leads may sense an irregularity in the beat to beat intervals of ventricular depolarizations. In one example embodiment, the sensor may record an electrical signal generated by the heart, such as from and intracardiac electrogram (IEGM). The sensor and/or TID controller 197 may subsequently use a signal-processing algorithm to determine the heart rhythm from the recorded electrical signal. It should be understood that there are many ways to detect and/or sense atrial tachycardia, and these examples are non-limiting.

Additionally or alternatively, TID controller 197 is configured to receive a signal from a user input device (e.g., user input device 150, shown in FIG. 1B). The signal includes patient input indicating the patient's status. TID controller 197 may use this received signal to determine whether to continue the session of TID therapy, adjust one or more parameters of the TID therapy, or cancel the session.

It has been shown that TID therapy is most beneficial to a patient when received in regular, periodic intervals, also referred to as a "schedule." When a TID therapy session must be cancelled due to an atrial tachycardia episode, particularly an AF episode, the benefits of the TID therapy may be reduced. Accordingly, TID controller 197 may be configured to monitor and track each TID therapy session to determine whether TID therapy was received for a predetermined minimum amount of time (e.g., a predetermined number of hours). If TID therapy was received for less than the predetermined minimum amount of time during a session, TID controller 197 may update a schedule of TID therapy to include an additional or replacement session. Alternatively, TID could be administered using the non-tracking ventricular pacing mode, as described above.

In some embodiments, TID controller 197 updates the schedule to increase a total number of TID therapy sessions if one or more sessions are cancelled. For example, an example schedule may include a session of TID therapy every night for six weeks. If a patient experiences atrial tachycardia nightly for a period of two weeks during the schedule and must cancel one or more sessions, TID controller 197 may update the schedule to include an additional two weeks of nightly sessions. In some cases, the schedule may require a certain minimum number of consecutive full sessions. If the patient experiences atrial tachycardia every other night for two weeks and must cancel one or more sessions, TID controller 197 may update the schedule to include however many additional sessions are needed to meet the requirement of the minimum number of consecutive full sessions.

In other embodiments, a patient may be able to tolerate less-intense TID therapy during an atrial tachycardia episode. In these cases, it may be beneficial to pause or adjust TID therapy during a session to avoid cancelling a session.

Figure 2:
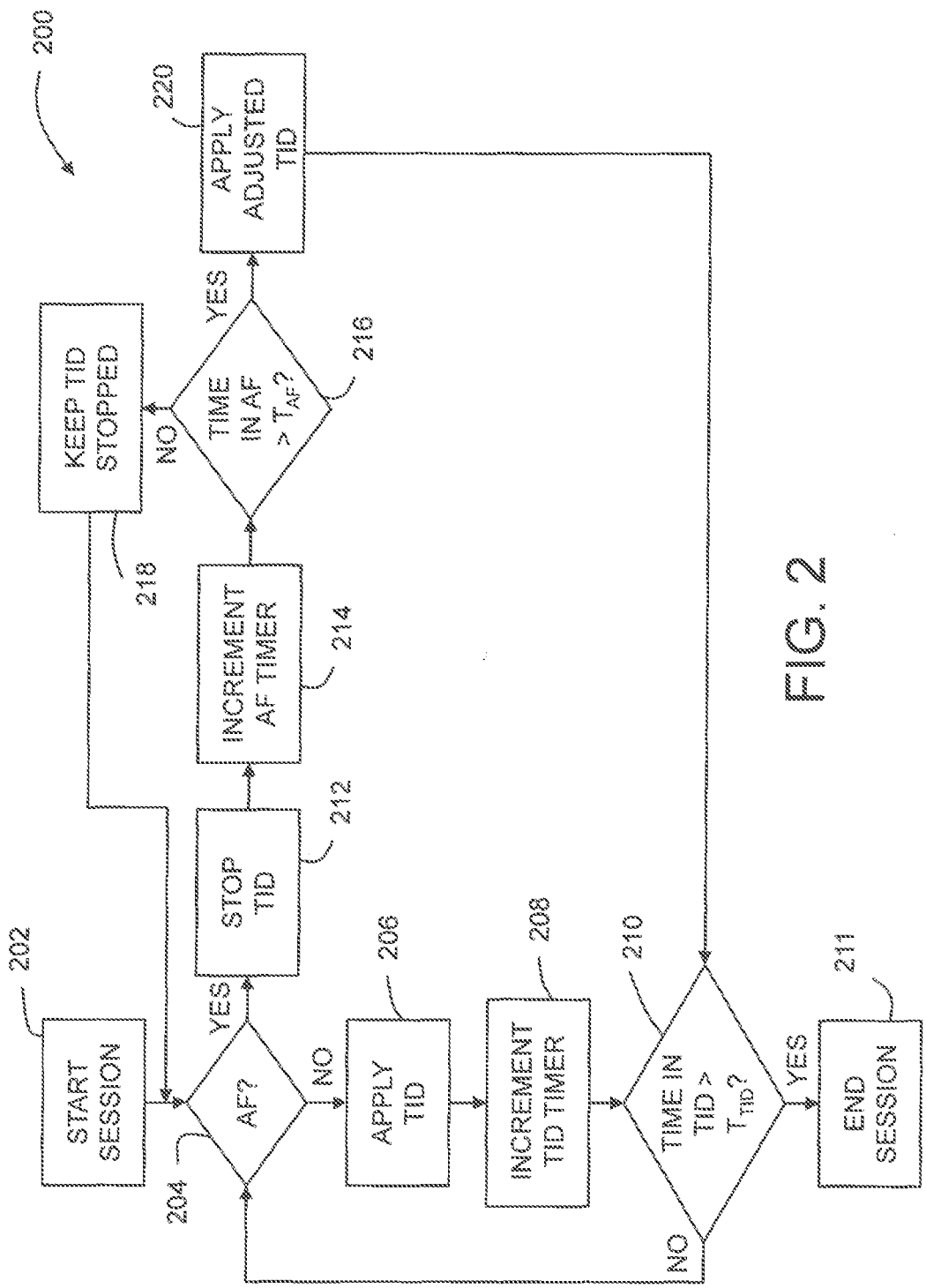
FIG. 2 is a flowchart of an example process of providing temporary induced dyssynchrony (TID) therapy to patients with atrial tachycardia.

FIG. 2 shows a flowchart of an example process 200 for providing TID therapy to a patient experiencing atrial tachycardia. In this example, the atrial tachycardia includes AF, but it should be understood that it may be equally applicable to cases where the atrial tachycardia includes atrial flutter. Process 200 may be implemented using pacemaker/ICD 100, specifically TID controller 197 (both shown in FIG. 1B). TID controller 197 initiates 202 a session of TID therapy. TID controller 197 monitors 204 the patient for an AF episode. For example, TID controller 197 may receive signal(s) from one or more sensors (e.g., sensor 108, shown in FIG. 1B) indicating whether or not the patient is experiencing AF. As described herein, receiving a signal from one or more sensors may include receiving an IEGM and/or a record of the heart's electrical signals, such that TID controller 197 may process the signals to determine the heart's rhythm.

When the patient is not experiencing AF, TID controller 197 applies 206 TID therapy. In one example embodiment, a first pacing mode, such as DDD pacing, may be applied 206 when the patient is not experiencing AF. DDD pacing includes sensing and pacing both the atrium and the ventricle. TID controller 197 identifies a predetermined minimum period of time for which TID therapy is to be applied 206 to the patient during a session, referred to as $T_{TID}$. For instance, a session may span six hours over a night, and a minimum of five hours within that session are to be spent applying 206 TID therapy. TID controller 197 then increments 208 a timer (e.g., a timer maintained by timing control circuitry 161, shown in FIG. 1B) to track the time spent applying 206 TID therapy. TID controller 197 monitors 210 (e.g., using timing control circuitry 161) the amount of time spent applying 206 TID therapy. If time spent applying 206 TID therapy is less than $T_{TID}$, TID controller 197 continues to monitor 204 for AF and continues to apply 206 TID therapy if no AF is detected. If time spent applying 206 TID therapy meets or exceeds $T_{TID}$, TID controller 197 may end 211 the session (i.e., stop applying TID therapy).

When TID controller 197 determines that the patient is experiencing AF based on monitoring 204, TID controller 197 may stop or pause 212 the application of TID therapy. TID controller 197 may additionally and substantially simultaneously initiate an AF timer (e.g., an AF timer maintained by timing control circuitry 161) to track the amount of time the patient spends experiencing AF. This AF timer may be understood to further represent an amount of time for which TID therapy is not being applied. TID controller 197 may identify a predetermined maximum period of time for which no TID therapy is to be applied during a session (e.g., one hour), or a predetermined maximum period of time for which TID therapy may be paused, referred to as $T_{AF}$. TID controller 197 increments 214 the AF timer, and monitors 216 the amount of time the patient experiences AF. If time spent experiencing AF is less than $T_{AF}$, TID controller 197 keeps 218 the TID therapy paused. When the time spent experiencing AF meets or exceeds $T_{AF}$, TID controller 197 applies 220 an adjusted TID therapy to accommodate the AF episode. For example, TID controller 197 may apply 220 TID therapy in an adjusted pacing mode, such as VVI pacing. VVI pacing includes only ventricular sensing and pacing. DDD pacing is based on atrial activity, whether paced or sensed, and AV delay is applied and the ventricle paced accordingly. When the patient is experiencing atrial tachycardia, specifically AF, the atria is beating very quickly, and it is not beneficial to pace the ventricle at the same speed. Accordingly, VVI pacing permits forced ventricular pacing independent of the atrial tachycardia.

TID controller 197 continues to monitor 204 the patient while applying 222 the adjusted TID therapy. If the AF episode ends, TID controller 197 may instead apply 206 the unadjusted TID therapy (e.g., DDD pacing) until $T_{TID}$ is met or exceeded. Alternatively, TID controller 197 may continue to apply 220 the adjusted TID therapy until $T_{TID}$ is met or exceeded.

The systems and methods described herein leverage the concept that beneficial effects of TID therapy are recognized when TID therapy is applied for regular, periodic intervals. Accordingly, providing TID therapy to accommodate a patient experiencing atrial tachycardia may facilitate achieving the full beneficial effects in patients' hearts.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable cardiac device for providing temporary induced dyssynchrony (TID) therapy to a patient with atrial tachycardia, the implantable cardiac device comprising:
a pulse generator;
a plurality of electrodes coupled to the pulse generator; and
a controller communicatively coupled to the pulse generator and configured to:
cause the pulse generator to deliver TID therapy to a patient's heart via the plurality of electrodes;
determine that the patient's heart is experiencing atrial tachycardia; and
adjust at least one parameter of the TID therapy based on the determination.

2. The implantable cardiac device of claim 1, wherein the controller is further configured to receive a signal from at least one sensor to determine that the patient's heart is experiencing atrial tachycardia.

3. The implantable cardiac device of claim 1, wherein the at least one parameter includes a pacing mode, the controller further configured to adjust the pacing mode to a non-atrial tracking ventricular pacing mode.

4. The implantable cardiac device of claim 3, wherein the at least one parameter further includes a pacing rate, the controller further configured to adjust the pacing rate to a higher pacing rate associated with the non-atrial tracking ventricular pacing mode.

5. The implantable cardiac device of claim 1, wherein the atrial tachycardia includes atrial flutter, and wherein the at least one parameter includes an atrioventricular (AV) delay, the controller further configured to reduce shortening of the AV delay.

6. The implantable cardiac device of claim 1, wherein the atrial tachycardia includes atrial fibrillation (AF), and wherein the controller comprises timing control circuitry, the controller further configured to:
upon determining the patient's heart is experiencing AF, cause the pulse generator to stop applying the TID therapy;
identify a predetermined maximum amount of time for the patient's heart to not be receiving the TID therapy; and
upon the timing control circuitry indicating the predetermined maximum amount of time has elapsed, cause the pulse generator to apply an adjusted TID therapy with the adjusted at least one parameter.

7. The implantable cardiac device of claim 6, wherein the controller is further configured to:
identify a predetermined minimum amount of time for applying any TID therapy to the patient's heart;
determine a remainder of the predetermined minimum amount of time; and
cause the pulse generator to apply at least one of the TID therapy and the adjusted TID therapy for the remainder of the predetermined minimum amount of time.

8. The implantable cardiac device of claim 7, wherein the controller is further configured to:
determine that the patient's heart is no longer experiencing AF; and
cause the pulse generator to apply the TID therapy to the patient's heart for the remainder of the predetermined minimum amount of time.

9. The implantable cardiac device of claim 1, wherein the controller is further configured to:
cause the plurality of electrodes to stop applying the TID therapy for a remainder of a session of TID therapy;
access a TID therapy schedule; and
update the TID therapy schedule to include a replacement session of TID therapy.

10. An implantable cardiac device comprising:
a pulse generator;
a plurality of electrodes coupled to the pulse generator;
a memory device; and
a processor communicatively coupled to the memory device, the processor configured to:
cause the pulse generator to apply temporary induced dyssynchrony (TID) therapy to a patient's heart via the plurality of electrodes;
determine that the patient's heart is experiencing atrial tachycardia; and
adjust at least one parameter of the TID therapy based on the determination.

11. The implantable cardiac device of claim 10, wherein the processor is further configured to receive a signal from at least one sensor to determine that the patient's heart is experiencing atrial tachycardia.

12. The implantable cardiac device of claim 10, wherein the at least one parameter includes a pacing mode, the processor further configured to adjust the pacing mode to a non-atrial tracking ventricular pacing mode.

13. The implantable cardiac device of claim 10, wherein the atrial tachycardia includes atrial flutter, and wherein the at least one parameter includes an atrioventricular (AV) delay, the processor further configured to reduce shortening of the AV delay.

14. The implantable cardiac device of claim 10, wherein the atrial tachycardia includes atrial fibrillation (AF), and wherein the processor comprises timing control circuitry, the processor further configured to:
upon determining the patient's heart is experiencing AF, cause the plurality of electrodes to stop applying the TID therapy;
identify a predetermined maximum amount of time for the patient's heart to not be receiving the TID therapy; and
upon the timing control circuitry indicating the predetermined maximum amount of time has elapsed, cause the pulse generator to apply an adjusted TID therapy with the adjusted at least one parameter.

15. The implantable cardiac device of claim 14, wherein the processor is further configured to:
identify a predetermined minimum amount of time for applying any TID therapy to the patient's heart;
determine a remainder of the predetermined minimum amount of time; and
cause the pulse generator to apply at least one of the TID therapy and the adjusted TID therapy for the remainder of the predetermined minimum amount of time.

16. The implantable cardiac device of claim 10, wherein the processor is further configured to:
cause the pulse generator to stop applying the TID therapy for a remainder of a session of TID therapy;
access a TID therapy schedule; and
update the TID therapy schedule to include a replacement session of TID therapy.

17. A method for providing temporary induced dyssynchrony (TID) therapy to a patient with atrial tachycardia, the method comprising:
delivering TID therapy to a patient's heart via a plurality of electrodes;
determining that the patient's heart is experiencing atrial tachycardia; and
adjusting at least one parameter of the TID therapy based on the determination.

18. The method of claim 17, wherein the at least one parameter includes a pacing mode, and wherein adjusting at least one parameter of the TID therapy comprises adjusting the pacing mode to a non-atrial tracking ventricular pacing mode.

19. The method of claim 17, wherein the atrial tachycardia includes atrial flutter, wherein the at least one parameter includes an atrioventricular (AV) delay, and wherein adjusting at least one parameter of the TID therapy comprises reducing shortening of the AV delay.

20. The method of claim 17 further comprising:
- upon determining the patient's heart is experiencing atrial tachycardia including atrial fibrillation, terminating application of the TID therapy;
- identifying a predetermined maximum amount of time for the patient's heart to not be receiving the TID therapy; and
- upon receiving an indication that the predetermined maximum amount of time has elapsed, applying an adjusted TID therapy with the adjusted at least one parameter.

* * * * *